United States Patent [19]

Woynar et al.

[11] Patent Number: 4,837,359

[45] Date of Patent: Jun. 6, 1989

[54] PROCESS FOR THE PRODUCTION OF POLYISOCYANATES WITH BIURET STRUCTURES

[75] Inventors: Helmut Woynar, Dormagen; Klaus König, Odenthal; Josef Pedain, Cologne, all of Fed. Rep. of Germany; William E. Slack, Moundsville, W. Va.

[73] Assignees: Bayer Aktiengesellschaft, Leverkusen, Fed. Rep. of Germany; Mobay Corporation, Pittsburgh, Pa.

[21] Appl. No.: 139,495

[22] Filed: Dec. 30, 1987

[30] Foreign Application Priority Data

Jan. 7, 1987 [DE] Fed. Rep. of Germany ....... 3700209

[51] Int. Cl.$^4$ .......................................... C07C 119/042
[52] U.S. Cl. .................................................... 560/335
[58] Field of Search .......................................... 560/335

[56] References Cited

U.S. PATENT DOCUMENTS 3,392,183  7/1968  Windemuth et al. .
3,903,126  9/1975  Woerner et al. .
4,147,714  4/1979  Hetzel et al. .
4,264,519  4/1981  Hennig et al. .

Primary Examiner—Alan Siegel
Attorney, Agent, or Firm—Gene Harsh; Joseph C. Gil; Richard E. L. Henderson

[57] ABSTRACT

Polyisocyanates with biuret structures are produced at temperatures above 250° C. More specifically, an excess of a diisocyanate having aliphatically and/or cycloaliphatically bound isocyanate groups is reacted with a diamine containing aliphatically and/or cycloaliphatically bound amino groups at temperatures above 250° C. for relatively brief periods of time. Water and/or polyvalent alcohols may optionally be included in the reaction mixture. The polyisocyanates with biuret structures produced by this process are characterized by good color, good dilutability with covalent solvents and comparatively low viscosity.

12 Claims, 1 Drawing Sheet

PROCESS FOR THE PRODUCTION OF POLYISOCYANATES WITH BIURET STRUCTURES

BACKGROUND OF THE INVENTION

The present invention relates to an improved process for the production of polyisocyanates with biuret structures.

The production of polyisocyanates with biuret structures by the direct reaction of excess amounts of organic diisocyanates with organic diamines at raised temperatures is known. For example, DE-OS No. 2,261,065 (Example 16) discloses the reaction of excess amounts of 1,6-diisocyanatohexane with 1,6-diaminohexane, during which the reactants are stirred for a period of 12 hours at 180° C. This extensive heating at a high temperature is not only uneconomic but leads to discoloration of the reaction product, particularly under large-scale production conditions. Use of this product is non-fade lacquers is therefore limited. In fact, even after the product of Example 16 of this disclosure was reworked, it was not possible to obtain a monomeric starting diisocyanate-free biuret polyisocyanate completely free of insoluble gel-like side products.

In the method disclosed in DE-OS 2,609,995, gaseous diamine is introduced into the already present diisocyanate at a temperature of from 100° to 250° C. No polyurethane precipitation occurs during this process and the reaction mixture is a clear solution at every point in time. This is achieved by the continuous dilution of the diamines introduced in gaseous form. Although this process allows the production of high-valency polyisocyanates with biuret structures, it is not suitable for carrying out on an industrial scale because of the large volumes of gaseous diamines necessary and the extremely critical control of the reaction conditions.

EP-B-3,505 discloses a process in which the diamine is introduced into the diisocyanate already present with the help of a smooth jet nozzle of defined size under excess pressure. Reaction temperatures of up to 250° C. may be used. Depending upon the reaction temperature, urea dispersions may form in excess starting diisocyanate during the process of this prior publication. Subsequent heat treatment converts such dispersions to solutions of biuret polyisocyanate in excess starting diisocyanate. One disadvantage of this process, in addition to the required use of special apparatus (smooth jet nozzle), is that the resulting polyisocyanates with biuret structures after the removal of the excess starting diisocyanate (in particular 1,6-diisocyanatohexane) have a considerable portion of higher oligomers and side products. This leads to an increase in the viscosity, an undesired decrease of the NCO content, and a worsened dilutability with covalent solvents.

SUMMARY OF THE INVENTION

It has now been discovered that it is possible to produce high-valency polyisocyanates with biuret structures based on aliphatic or cycloaliphatic diisocyanates or diamines without the use of special mixing apparatus. This is achieved if the starting materials are brought to a reaction with each other at a temperature above 250° C., preferably above 270° C. This discovery is particularly surprising in view of the accepted opinion that reaction temperatures above 250° C. should be avoided as far as possible, in order to prevent undesired discoloring of the reaction product (See, eg., DE-OS No. 2,609,995).

The present invention makes possible the continuous production of polyisocyanates with biuret structures by continuous reaction of excess amounts of organic diisocyanates with exclusively aliphatically and/or cycloaliphatically bound isocyanate groups with organic diamines with exclusively aliphatically and/or cycloaliphatically bound primary amino groups at a raised temperature. In this process the reaction partners are brought to reaction at a temperature above 250° C.

DETAILED DESCRIPTION OF THE INVENTION

Figure 1:
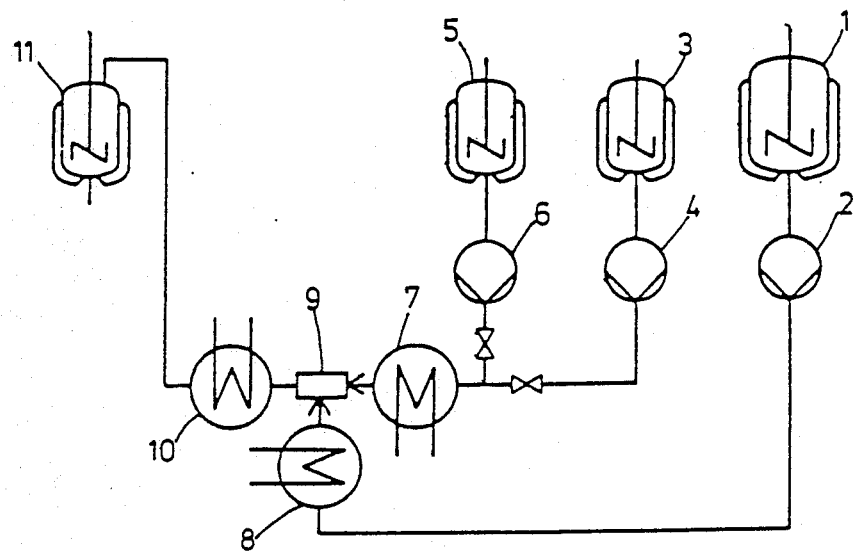
FIG. 1 is a schematic illustration of an apparatus useful in carrying out the process of the present invention.

The present invention relates to a process for the production of a polyisocyanate containing a biuret structure. In this process, excess organic diisocyanate containing aliphatically and/or cycloaliphatically bound isocyanate groups is reacted with an organic diamine containing aliphatically and/or cycloaliphatically bound primary amino groups at a temperature above 250° C.

Starting materials for the process of the present invention are organic diisocyanates with exclusively aliphatically and/or cycloaliphatically bound isocyanate groups having a molecular weight below 300. Examples of such diisocyanates include 1,4-diisocyanatobutane, 1,6-diisocyanatohexane, 1,6-diisocyanato-2,2,4-trimethyl-hexane, 1,6-diisocyanato-2,4,4-trimethylhexane, 2,6-diisocyanatocaproic acid ethyl ester, 1,12-diisocyanatododecane, 1,4-diisocyanatocyclohexane, 1-isocyanato-3,3,5-trimethyl-5-isocyanatomethylcyclohexane, 4,4'-diisocyanatodicyclohexylmethane and 6-isocyanatocaproic acid-2-isocyanato ethyl ester. Any mixtures of such diisocyanates may also be used. 1,6-diisocyanatohexane is particularly preferred.

The organic diamine starting materials for the process of the present invention are organic diamines having exclusively aliphatically and/or cycloaliphatically bound primary amino groups having a molecular weight below 300. Examples include 1,2-diaminoethane, 1,2-diaminopropane, 1,3-diaminopropane, 1,4-diaminobutane, 1,6-diaminohexane, 1,6-diamino-2,2,4-trimethylhexane, 1,6-diamino-2,4,4-trimethylhexane, 1,4-diaminohexane, 1-amino-3,3,5-trimethyl-5-aminomethylcyclohexane and 1,4,4'-diamino-dicyclohexylmethane. Any mixtures of such diamines may also be used. 1,6-diaminohexane is particularly preferred.

In the process according to the invention, the diamine(s) can also be used in admixture with water and/or polyvalent aliphatic alcohols of a molecular weight below 500. Suitable polyvalent alcohols include 1,4-dihydroxybutane, neopentyl glycol, 1,6-dihydroxyhexane, 1,3-dihydroxy-2-ethyl-hexane, 1,6-dihydroxy-2,2,4-trimethylhexane, 1,6-dihydroxy-2,4,4-trimethylhexane, trimethylolpropane, glycerine, and short-chain hydroxy-functional polyesters of such simple polyols and deficient amounts of aliphatic dicarboxylic acids such as adipinic acid, succinic acid and azelaic acid. Low molecular weight polycaprolactones with hydroxyl groups, started on the simple polyols given in the examples are also suitable. Any mixtures of such polyvalent alcohols can also be used.

The coincidental use of water and/or polyvalent alcohols is however, less desirable. If such additional starting materials are used, they should be employed in quantities of maximally 0.2 mols of water per mol of diamine and/or maximally 1, preferably 0.5 mols of polyvalent alcohol per mol of diamine.

During the process of the present invention, the starting diisocyanate and the diamine(s) or the mixtures of diamine(s) with water and/or polyvalent alcohols are continuously brought to reaction in quantities corresponding to an equivalent ratio of isocyanate groups to amino groups of at least 4:1, preferably of 4:1 to 25:1 and most preferably of 7:1 to 20:1 with the primary amino groups being considered as monofunctional groups for purposes of such calculation.

It is essential to the invention that the starting materials be brought to reaction with each other at a temperature above 250° C., preferably above 270° C., especially between 270° and 320° C. immediately after being thoroughly mixed. These high reaction temperatures at the beginning of the reaction may be achieved by preheating of the diisocyanate to temperatures above 180° C., preferably above 220° C. In the case where a large excess of diisocyanate is used, pre-heating of the diamines or the mixtures of diamine and water and/or polyvalent alcohol is often unnecessary. Generally, however, the diamine or mixture of diamine and water and/or polyvalent alcohol is also pre-heated to about 50° to 200° C. It can normally be assumed that the reaction mixture heats up, even without heating the mixing vessel, to a temperature of approximately 20° to 70° C. above the temperature that can be expected due to heating up of the starting materials because of the high heat of reaction of the spontaneous resulting reaction. The heating temperatures of the starting materials necessary for securing the high temperatures essential to the invention can be estimated to a good approximation from the specific heat of the starting materials (about 0.5 kcal/kg ° K.), and the reaction enthalpy of the reaction (about 35 kcal/mol). They may also be determined, if necessary, by a simple preliminary experiment.

The heating of the diisocyanate(s) must be carried out in as short a period of time as possible, preferably within a period of less than 30 seconds, because of the known temperature-sensitivity of these compounds. This rapid heating may be accomplished by the use of corresponding heat exchange aggregates of the state of the art. The heat exchangers useful in the practice of the present invention include shell—and—tube exchangers, bundle exchangers and plate exchangers. They can be run on a fluid heating medium, with superheated steam or by a direct electrical heating. The use of heat exchangers that allow the heating process of the original diisocyanate within a time span of less than 3 seconds is particularly preferred.

The continuous streams of the reaction partners are combined in a mixing chamber after pre-heating. In the process according to the invention, no particular demands are placed upon the capacity of the mixing chamber with respect to an intensive mixing of the components. Any static or dynamic aggregates known to those skilled in the art can be used. In general, a simple reaction pipe without any baffles, to one end of which the reaction components are brought in direct current, is completely sufficient and is also preferable.

The points of entry of the components are preferably in the form of perforated screens or nozzles, so that the dosage can take place under raised pressure. Such means ensure that the reaction mixture does not reach the diisocyanate and diamine feed stock. To this end the cross-sections are chosen so that in each case a pressure of 1.5 to 100 bars, preferably of 1.5 to 40 bars builds up on the feeding mains. The form and arrangement of the nozzles and/or perforated screens as well as high pressure are not essential to the invention.

The volume of the mixing chamber and of any cooling area or chamber as well as the intensity of cooling in the cooling area or chamber must be chosen so that the average residence period of the reaction mixture from combination of the starting components to reduction of the temperature below 250° C. is maximally 60 second, preferably no more than 30 seconds and, most preferably no more than 10 seconds. In the process of the present invention, the average residence period of the reaction mixture at the preferred temperatures of above 270° C. is in general at most 20 seconds, preferably at most 10 seconds and, most preferably, at most 1 second.

After running through the mixing chamber and any cooling area or chamber, the reaction mixture is continuously cooled by a suitable heat exchanger within 10 minutes at the most, preferably 5 minutes at most, gradually or step-wise to a temperature of from 80° to 220° C. (preferably 120° to 200° C.) and subjected at these temperatures to a thermal after-treatment by means of a suitable after-reactor, preferably for a residence period of no more than 5 hours, more preferably no more than 2 hours, most preferably up to 30 minutes. It is essential that the reaction mixture be subjected to temperatures of over 250° C. only within the above mentioned short periods of time. The duration of the thermal after-treatment may however vary within wide limits. In general, at the lower temperatures within the 80°–220° C. temperature range, a comparatively long thermal after-treatment is desirable. At the higher temperatures, a comparatively short thermal after-treatment is desirable.

The thermal after-treatment can be carried out for example in reactors arranged in cascade or in stirrer vessels through which there is a continuous stream.

Subsequent to the thermal after-treatment, a reaction product is present as a solution of polyisocyanate with biuret groups in excess starting diisocyanate. This solution can be freed of excess starting diisocyanate immediately after the thermal after-treatment or at a later point in time by distillation or by extraction for example with n-hexane. In this manner high-valency polyisocyanates with biuret structures may be obtained, with a maximum content of excess starting diisocyanate of 0.7 per cent by weight, preferably 0.3 per cent by weight.

The polyisocyanates with biuret groups produced by the method of the present invention, especially those that have been produced by the exclusive use of 1,6-diisocyanato-hexane and 1,6-diamino-hexane as starting materials, represent valuable starting materials for the production of two component polyurethane lacquers. The products of the present invention are distinguished by their good color numbers, good dilutability with nonpolar solvents and comparatively low viscosity.

Use of water and especially of low molecular weight polyvalent alcohols such as those mentioned as examples above to incorporate urethane or allophanate groupings in the products makes it possible to modify the flexibility, bonding, hydrolysis stability, hardness and/or solvent stability of the polyisocyanates and the coatings produced from them.

The percentages given in the examples that follow are percentages by weight.

EXAMPLES

The apparatus illustrated in FIG. 1 was used in each of the following examples.

In FIG. 1,
1 represents a stirrer container for diisocyanate,
2 represents a feed pump for diisocyanate,
3 represents a stirrer container for diamine,
4 represents a feed pump for diamine,
5 represents a stirrer container for auxiliary solvents,
6 represents a feed pump for auxiliary solvents,
7 represents a heat exchanger for heating diamine and auxiliary solvents,
8 represents a heat exchanger for heating diisocyanate,
9 represents the mixing chamber,
10 represents a heat exchanger for cooling the reaction mixture and
11 represents an impeller type mixer for products of the process.

The auxiliary solvents (e.g. diphenylether from container 5) were only used at the beginning for running in the continuously driven apparatus and led together with the diisocyanate into the mixing chamber, in order to produce constant temperature conditions, by which means it was ensured that no back-mixing of the components in the feeding streams could occur. The actual starting of the apparatus was achieved simply and safely by switching over from the solvent stream to the diamine stream. There were nozzles before the entrance of the streams for diisocyanate and diamine into the mixing chamber, in order to achieve high flow speeds at this point. In principle, the shape of these nozzles may be freely chosen, as the nozzles do not have the task of introducing mixing energy into the reaction solution, but only of reliably hindering back-mixing.

Immediately after leaving the mixing chamber, the reaction mixture was cooled to the lower temperature level by heat exchanger 10 within the residence periods given in the examples. The thermal after-treatment of the reaction products occurred in the impeller type mixer 11 having a continuous in-out flow. Such after-treatment could also have been carried out in a stirring pot cascade or in a residence area of corresponding size.

Glass containers were used as stirrer vessels 1, 3, 5 and 11. Piston dosing pumps (LEWA) were used as pumps 2, 4 and 6.

Twin pipe heat exchangers were used as heat exchangers 7 and 8, driven by oil as a heat transfer medium, with the following dimensions:

|  | 8 | 7 |
|---|---|---|
| Inner volume of the heat exchanger | 22.8 cm$^3$ | 0.4 cm$^3$ |
| Heat exchanger surface area | 415 cm$^3$ | 31.5 cm$^3$ |

The desired short residence periods at high temperatures were achieved with these dimensions.

The mixing chamber 9 was formed as a cylindrical pipe with a nozzle opening of 0.1 mm diameter for the diamine and two nozzle openings of 0.5 mm diameter for the diisocyanate at the entrance end and dimensions of 5 cms length by 4 mm diameter. The volume was 0.6 cm$^3$. The heat exchanger 10 directly connected to the mixing chamber also took the form of a pipe heat exchanger of variable volume and offered the possibility of tempering various sections differently. The exact conditions are given separately in the individual examples.

EXAMPLE 1

1,6-diisocyanato-hexane (HDI) and 1,6-diaminohexane (HDA) were introduced to the vessels 1 and 3 at 70° C. Diphenylether was introduced into container 5 as an inert solvent, also at about 70° C. After a running in period of 15 minutes, during which 338 g/min HDI and 20.0 g/min auxiliary solvent (instead of HDA) were heated through the heat exchangers 7 and 8 to temperatures of 240° C. (HDI) and 190° C. (auxiliary solvent) and driven into the mixing chamber, the inflow of auxiliary solvent was cut off. 20.3 kg of HDI per hour (=120.8 mol/h) were heated with 1.18 kg HDA per hour (=10.17 mol/h) over the heat exchangers 7 and 8 to temperatures of 240° C. (HDI) and 190° C. (HDA) and driven into the mixing chamber. The mixing chamber adjusted to a temperature of 285° C. The average residence period at this temperature from the entrance of the feeding main into the mixing chamber until the entrance into the heat exchanger 10 was around 0.5 seconds. The reaction mixture leaving the mixing chamber at a temperature of 285° C. was then cooled down to 140° C. in the heat exchanger 10. The average residence time in this heat exchanger was 4 minutes. The time span from entering the cooler 10 to falling below a temperature of 250° C. was about 4 seconds. The reaction mixture was then stirred in the stirrer vessel 11 for an average residence period of 1 hour at 140° C. The product of the process continuously leaving the stirrer vessel 11 (21.48 kg/h) had an NCO content of 39.4%. After the removal of excess HDI by means of a thin film evaporator (not shown) down to a residual content of 0.3%, 357 g of a polyisocyanate with biuret groups per kg of crude solution, with the following characteristics:

| NCO content | 22.7% |
|---|---|
| Viscosity (23° C.) | 5870 mPas |
| APHA color number | 70–90 | were obtained.

EXAMPLE 2

Using the same procedure described in Example 1, 21.2 kg/h (=126 mol/h) HDI were reacted with 0.812 kg/h (=7.0 mol/h) HDA, i.e. at a molar ratio of 18:1, under the following conditions:
Temperature of HDI before the reaction: 260° C.
Temperature of HDA before the reaction: 140° C.
Temperature in the mixing chamber: 290° C.
Average residence time at 290° C.: 0.5 seconds After leaving the mixing chamber, the mixture was cooled down to 160° C. within 3 minutes, where the time span (average residence time) from entering the cooler 10 to falling below a temperature of 250° C. was about 4 seconds, and subsequently stirred for another 30 minutes at this temperature.

22.12 kg/h of a "crude biuret solution" with an NCO content of 41.8% were obtained, which, after removal of excess HDI down to a residual content of 0.2% yielded 280 g per kg of crude solution of a polyisocyanate with the following characteristics:

| NCO content | 23.1% |
|---|---|
| Viscosity (23° C.) | 2450 mPas |
| APHA Color number | 110-130 |

EXAMPLE 3

Using the same procedure described in Example 1, 19.2 kg/h (=114.3 mols/h) HDI were reacted with 1.33 kg/h (=11.4 mols/h) HDA, i.e. at a molar ratio of 10:1, under the following conditions:
Temperature of HDI before the reaction: 220° C.
Temperature of HDA before the reaction: 160° C.
Temperature in the mixing chamber: 278° C.
Average residence time at 278° C.: 0.5 seconds The reaction mixture leaving the mixing chamber was cooled to 120° C. within 5 min and subsequently stirred for another 4 hours at this temperature. In this process, the time span (average residence time) from entering the cooler 10 to falling below a temperature of 250° C. was 5 seconds.

20.53 kg/h of a "crude biuret solution" with an NCO content of 36.8% were obtained. After removal of the excess HDI (down to a residual content of 0.1%) 460 g of a polyisocyanate per kg crude solution with the following characteristics:

| NCO content | 21.7% |
|---|---|
| Viscosity (23° C.) | 10,500 mPas |
| APHA color number | 60-70 | were obtained.

EXAMPLE 4

Using the procedure described in Example 1, 14.6 kg/h (=86.9 mol/h) HDI were reacted with 1.07 kg/h of a mixture of 3 molar pats HDA and 1 molar part 2,2-dimethyl-propanediol-1,3 under the following conditions:
Temperature of HDI before the reaction: 243° C.
Temperature of HDA/neopentyl glycol mixture before the reaction: 190° C.
Temperature in the mixing chamber: 272° C.
Average residence period at 272° C.: about 0.7 sec.

After leaving the mixing chamber, the mixture was cooled down to 145° C. within 3 minutes and subsequently stirred for another 30 minutes at this temperature. In this process, the time span (average residence period) from entering the cooler 10 to falling below a temperature of 250° C. was about 4 seconds.

15.67 kg/h of a crude solution containing biuret, urethane and allophanate groups which an NCO content of 35.8% were obtained, which, after removal of the excess HDI down to a residual content of 0.3%, yielded 413 g of a polyisocyanate per kg crude solution, with the following characteristics:

| NCO content | 20.7% |
|---|---|
| Viscosity (23° C.) | 18,900 mPas |
| APHA color number | 180 |

EXAMPLE 5

Using the procedure described in Example 1, 15.0 kg/h (=89.3 mol/h) were reacted with 1.099 kg/h of a mixture of 95 molar parts of HDA and 5 molar parts water under the following conditions:
Temperature of HDA before the reaction: 240° C.
Temperature of HDI/H$_2$O-mixture before the reaction: 190° C.
Temperature in the mixing chamber: 295° C.
Average residence time at 290° C.: about 0.6 seconds.

After leaving the mixing chamber, the mixture was cooled down to 160° C. within 2 minutes and subsequently stirred for another 15 minutes at this temperature. In this process, the time span (average residence period) from entering the cooler 10 to falling below a temperature of 250° C. was about 6 seconds.

16.0 kg/h of a "crude biuret solution" with an NCO content of 35.1% were obtained, which, after removal of the excess HDI down to a residual content of 0.2%, yielded 536 g of a polyisocyanate per kg crude solution, with the following characteristics:

| NCO content | 21.3% |
|---|---|
| Viscosity (23° C.) | 30,000 mPas |
| APHA color number | 110-130 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a polyisocyanate containing a biuret structure comprising reacting
   (a) an excess of an organic diisocyanate containing aliphatically and/or cycloaliphatically bound isocyanate groups with
   (b) an organic diamine containing aliphatically and/or cycloaliphatically bound primary amino groups in a reactor at a temperature above 270° C.

2. The process of claim 1 in which the reaction is carried out on a continuous basis.

3. The process of claim 1 in which the reactants are present in the reactor for an average residence time of no more than 60 seconds.

4. The process of claim 1 in which the reactants are present in the reactor for an average residence time of no more than 20 seconds.

5. The process of claim 1 in which the organic diamine is used in admixture with water and/or a polyvalent aliphatic alcohol having a molecular weight below 500.

6. The process of claim 1 in which the organic diamine is used in admixture with up to 0.2 mol water and/or up to 1 mol polyvalent alcohol having a molecular weight below 500 per mol of diamine.

7. The process of claim 1 in which the organic diisocyanate is 1,6-diisocyanato-hexane.

8. The process of claim 7 in which the organic diamine is 1,6-diamino-hexane.

9. The process of claim 1 in which the organic diamine is 1,6-diamino-hexane.

10. The process of claim 1 which further comprises cooling the reaction mixture to a temperature of from 80° to 220° C. within 10 minutes.

11. The process of claim 10 which further comprises removing unreacted diisocyanate (a) from the reaction mixture by distillation.

12. The process of claim 1 which further comprises removing unreacted diisocyanate (a) from the reaction mixture by distillation.

* * * * *